(12) United States Patent
Paul

(10) Patent No.: US 7,137,997 B2
(45) Date of Patent: Nov. 21, 2006

(54) SPINAL FUSION IMPLANT

(75) Inventor: David C. Paul, Phoenixville, PA (US)

(73) Assignee: Globus Medical, Inc., Audobon, PA (US)

( * ) Notice: Subject to any disclaimer, the term of this patent is extended or adjusted under 35 U.S.C. 154(b) by 0 days.

(21) Appl. No.: 10/745,668

(22) Filed: Dec. 29, 2003

(65) Prior Publication Data

US 2005/0143822 A1     Jun. 30, 2005

(51) Int. Cl.
*A61F 2/44*      (2006.01)

(52) U.S. Cl. ................................... 623/17.11

(58) Field of Classification Search ............ 623/17.11, 623/17.16
See application file for complete search history.

(56) References Cited

U.S. PATENT DOCUMENTS

| | | |
|---|---|---|
| 4,759,769 A | 7/1988 | Hedman et al. |
| 5,306,309 A | 4/1994 | Wagner et al. |
| 5,458,643 A | 10/1995 | Oka et al. |
| 5,674,294 A | 10/1997 | Bainville et al. |
| 5,683,465 A | 11/1997 | Shinn et al. |
| 5,893,889 A | 4/1999 | Harrington |
| 6,245,108 B1 | 6/2001 | Biscup |
| 6,520,933 B1 | 2/2003 | Evans et al. |
| 6,547,823 B1 | 4/2003 | Scarborough et al. |
| 6,613,090 B1 | 9/2003 | Fuss et al. |
| 2002/0019637 A1* | 2/2002 | Frey et al. ................ 606/85 |
| 2002/0165612 A1 | 11/2002 | Gerber et al. |
| 2003/0100950 A1* | 5/2003 | Moret ................ 623/17.16 |
| 2004/0122518 A1* | 6/2004 | Rhoda ................ 623/17.11 |
| 2005/0288788 A1* | 12/2005 | Dougherty-Shah ....... 623/17.11 |
| 2006/0106460 A1* | 5/2006 | Messerli et al. ......... 623/17.11 |

* cited by examiner

*Primary Examiner*—Bruce Snow
(74) *Attorney, Agent, or Firm*—Castellano, Malm, Ferrario & Buck PLLC

(57) ABSTRACT

The present invention relates to spacers that are configured to promote fusion. Windows or openings in the sidewalls of the fusion spacers may be provided to allow a physician to view the treated area to confirm that fusion has occurred or to check on the progress of treatment. Fusion spacers of the invention may have two or more pairs of openings or windows that allow viewing of the treated area from different perspectives.

17 Claims, 8 Drawing Sheets

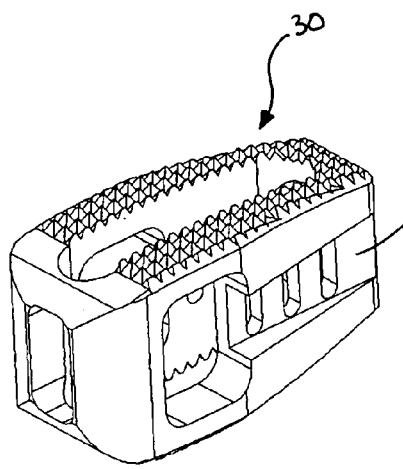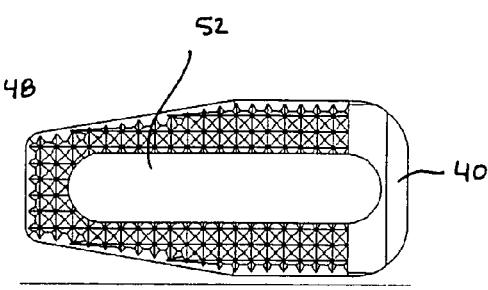
FIG. 6             FIG. 7A
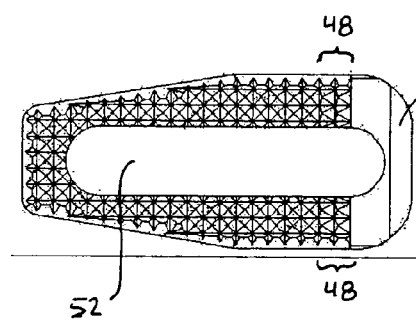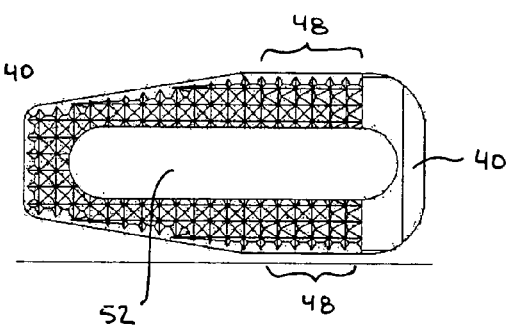
FIG. 7B             FIG. 7C

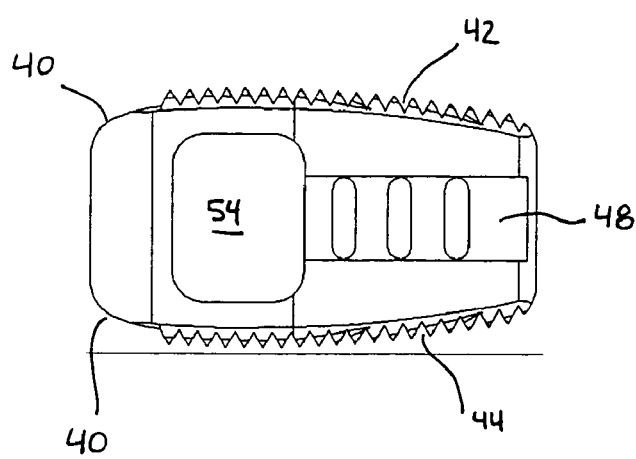
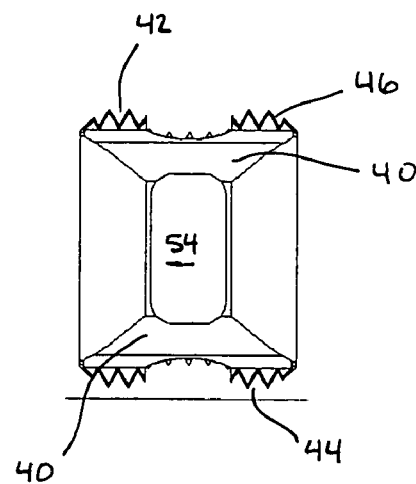
FIG. 8            FIG. 9
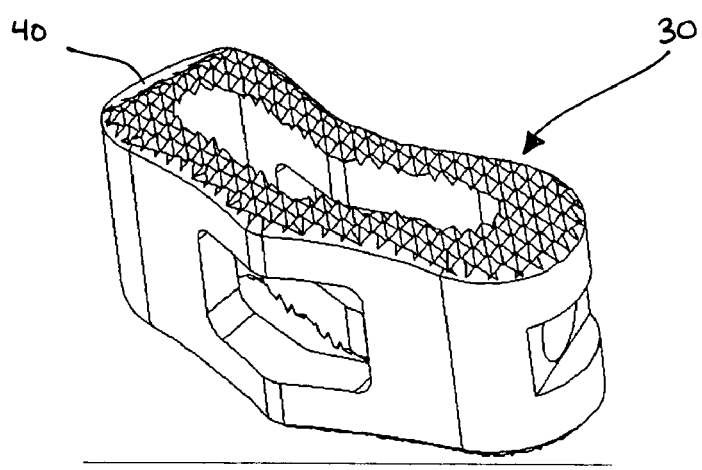
FIG. 10

SPINAL FUSION IMPLANT

FIELD OF THE INVENTION

The present invention relates to spacers for fusing vertebral bodies.

BACKGROUND OF THE INVENTION

The vertebrate spine is the axis of the skeleton on which all of the body parts "hang". In humans, the normal spine has seven cervical, twelve thoracic and five lumbar segments. The lumbar spine sits upon the sacrum, which then attaches to the pelvis, and in turn is supported by the hip and leg bones. The bony vertebral bodies of the spine are separated by intervertebral discs, which act as joints but allow known degrees of flexion, extension, lateral bending, and axial rotation.

The typical vertebra has a thick anterior bone mass called the vertebral body, with a neural (vertebral) arch that arises from the posterior surface of the vertebral body. The centra of adjacent vertebrae are supported by intervertebral discs. Each neural arch combines with the posterior surface of the vertebral body and encloses a vertebral foramen. The vertebral foramina of adjacent vertebrae are aligned to form a vertebral canal, through which the spinal sac, cord and nerve rootlets pass. The portion of the neural arch which extends posteriorly and acts to protect the spinal cord's posterior side is known as the lamina. Projecting from the posterior region of the neural arch is the spinous process.

The intervertebral disc primarily serves as a mechanical cushion permitting controlled motion between vertebral segments of the axial skeleton. The normal disc is a unique, mixed structure, comprised of three component tissues: the nucleus pulpous ("nucleus"), the annulus fibrosus ("anulus") and two vertebral end plates. The two vertebral end plates are composed of thin cartilage overlying a thin layer of hard, cortical bone which attaches to the spongy, richly vascular, cancellous bone of the vertebral body. The end plates thus act to attach adjacent vertebrae to the disc. In other words, a transitional zone is created by the end plates between the malleable disc and the bony vertebrae.

The spinal disc and/or vertebral bodies may be displaced or damaged due to trauma, disease, degenerative defects, or wear over an extended period of time. One result of this displacement or damage to a spinal disc or vertebral body may be chronic back pain.

A disc herniation occurs when the anulus fibers are weakened or torn and the inner tissue of the nucleus becomes permanently bulged, distended, or extruded out of its normal, internal anulus confines. The mass of a herniated or "slipped" nucleus tissue can compress a spinal nerve, resulting in leg pain, loss of muscle control, or even paralysis. Alternatively, with discal degeneration, the nucleus loses its water binding ability and deflates, as though the air had been let out of a tire. Subsequently, the height of the nucleus decreases causing the anulus to buckle in areas where the laminated plies are loosely bonded. As these overlapping laminated plies of the anulus begin to buckle and separate, either circumferential or radial anular tears may occur, which may contribute to persistent or disabling back pain. Adjacent, ancillary spinal facet joints will also be forced into an overriding position, which may create additional back pain.

Whenever the nucleus tissue is herniated or removed by surgery, the disc space will narrow and may lose much of its normal stability. In many cases, to alleviate back pain from degenerated or herniated discs, the disc is removed along with all or part of at least one neighboring vertebrae and is replaced by an implant that promotes fusion of the remaining bony anatomy. Some examples of such implants include those described in U.S. Pat. Nos. 6,520,993, 5,893,889, 5,683,465, 5,674,294, 5,458,643, 5,306,309, and 4,579,769.

While this treatment may help alleviate the pain once the vertebrae have been successfully fused together, there remains the possibility that the surgical procedure may not successfully or fully bring about the intended fusion. The success or failure of spinal fusion may depend upon several factors. For instance, the spacer—or implant or cage—used to fill the space left by the removed disc and bony anatomy must be sufficiently strong to support the spine under a wide range of loading conditions. The spacer should also be configured so that it is likely to remain in place once it has been positioned in the spine by the surgeon. Additionally, the material used for the spacer should be a biocompatible material and should have a configuration that promotes bony ingrowth.

As a result, the design of the implant should provide sufficient rigidity and strength to resist deformation when loading forces are applied to it. Likewise, the implant should sufficiently resist sliding or movement of the implant as a result of torsional or shearing loads. Often, these parameters lead designers to select predominantly solid structures made of bone or of radio opaque materials such as titanium.

For example, U.S. Pat. No. 6,547,823 describes an intervertebral implant made of cortical ring cut from a diaphysis of a long bone. The implant is generally solid with a through-hole extending from the top surface of the implant to the bottom surface.

U.S. Pat. No. 6,245,108 likewise illustrates how the design parameters described above often lead to a predominantly solid structure. The patent describes an interbody fusion implant having a top, bottom, front, back, and sides. A large through-hole is provided from the top surface to the bottom, while the front, back, and sides only have substantially smaller openings.

While it is generally known that providing a through-hole from the top to bottom surfaces helps promote bone growth in the treated area, the structure of the front, back, and side walls often substantially obscure or do not permit confirmation that fusion is taking place as desired. This difficulty of subsequently confirming that fusion is adequately taking place is particularly problematic when the spacer is made of radio opaque materials. Thus, while the use of radio opaque materials can be beneficial for providing greater structural rigidity of the spacer and for helping the physician to identify the position of the implant during insertion, these materials can have the disadvantage of limiting the ability to later confirm the implant has served its intended purpose of fusing the treated area.

Another disadvantage that results from prior art spacer designs is that of solid sidewalls or sidewalls with limited openings limits fusion of the treated area principally to the opening on the upper and lower sides of the spacer, if one is provided. Thus, while a spacer having an essentially closed or solid structure may maintain rigidity of the spacer, it does not provide optimal conditions for fusion to take place.

Instrumentation and specialized tools for insertion of an intervertebral implant is yet another design parameter to consider when designing a spacer. Spinal fusion procedures can present several challenges because of the small clearances around the spacer when it is being inserted into position. For instance, the instrumentation used may securely grip the implant on opposing sides or surfaces. In U.S. Pat. No. 6,520,933, for example, the superior and inferior surfaces have one or more regions in which no gripping teeth are present. These protrusion-free zones enable the implant to be grasped and manipulated by elongate rectangular blades. Notably, these protrusion-free zones are not formed as channels cut into the surface of the implant in order to maintain the strength and integrity of the implant so that it is less prone to failure. Thus, the clearance required in order to insert the spacer must be higher than the spacer itself in order to accommodate the instrumentation of the '933 patent. For this reason, distraction of the treated area typically is greater than the implant itself.

Similarly, when the gripping tools used to manipulate and insert the implant are on the sides of the spacer, additional clearance typically is needed in order to accommodate the added width of the insertion tool blades. Such increases in height or width of the profile of the spacer when coupled or in communication with instrumentation means that additional space is needed in order to insert the spacer. In some circumstances, providing for this additional clearance space can be difficult to achieve.

Thus, despite known devices that promote fusion of a treated area of the spine, there remains a need for spacer designs that optimize bony ingrowth, have structural rigidity to support the spine under a variety of loading conditions, allow for insertion through a lower profile, and provide for confirmation of the fusion process from a multiplicity of views.

BRIEF DESCRIPTION OF THE DRAWINGS

FIG. 6 is a perspective view of another embodiment of a fusion spacer according to the present invention;

FIGS. 7A–C are variations of top plan views of the fusion spacer of FIG. 6;

FIG. 8 is a lateral view of the fusion spacer of FIG. 6;

FIG. 9 is an anterior view of the fusion spacer of FIG. 6;

FIG. 10 is a perspective view of another embodiment of a fusion spacer according to the present invention;

DETAILED DESCRIPTION OF THE INVENTION

Figure 1:
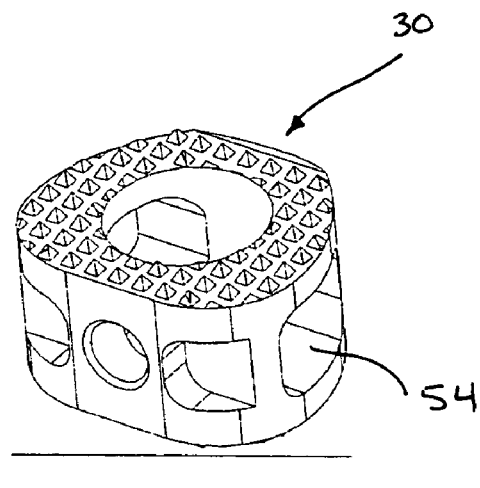
FIG. 1 is a perspective view of one embodiment of a fusion spacer according to the present invention.

The present invention relates generally to implantable spacers 30 that can be used to fuse together a treated area of the spine while restoring or maintaining the proper spacing and natural curvature of the spine. The treated area may include regions between adjacent vertebral bodies so that the height of the spacer corresponds approximately to the height of the disc. More preferably, however, the height of the spacer of the present invention is greater than the height of a disc alone. For instance, the treated area of the spine may be prepared by the physician by removing all or part of at least one vertebral body.

As explained in greater detail below, several features of the invention allow for more efficient insertion or placement of the spacers into a desired position. Additionally, the present invention also provides suitable rigidity and integrity for supporting the spine during fusion while also providing greater ability to confirm that fusion is taking place as desired.

One feature of the present invention that helps provide more efficient insertion of the spacer is the use of a chamfered or tapered lip 40. In general, the upper and lower surfaces 42, 44 of spacers 30 of the present invention have a plurality of teeth or protrusions 46 that engage with the bony surface of the vertebral bodies in or near the treated area. These protrusions 46 may be formed integrally with the upper and lower surfaces 42, 44 of the spacer 30 and may vary in profile, distribution, size, and number. Ultimately, the configuration of the protrusions or teeth 46 should be sufficient to securely hold the spacer 30 in the treated area after surgery while the treated area heals and undergoes fusion.

As the spacer 30 is being inserted into the treated area, one or more portions or edges of the spacer may act as a leading edge that helps distract anatomy near the treated area. For instance, a portion of the upper and lower surfaces 42, 44 of the spacer 30 that forms approximately the first 1 mm to 5 mm of the surface along the direction of travel the spacer may undergo greater compressive loading than the remainder of the upper and lower surfaces during insertion. If protrusions or teeth are disposed on these leading edges, they can prematurely grip and possibly cut or tear the nearby anatomy, thereby making insertion of the spacer 30 more difficult and potentially more harmful or painful to the patient.

The leading edges of spacers according to the present invention may have a chamfered or tapered lip 40 that is substantially or completely free of protrusions. As the spacer is inserted into the treated area, the lip 40 may help distract the bony anatomy with substantially less effort. Also, as the spacer moves toward its desired position, the lip 40 allows the spacer 30 to slide over the nearby anatomy with minimal cutting or tearing of tissue. As explained in greater detail below, in some embodiments of the invention two or more chamfered or tapered lips may be disposed on the spacer to facilitate even more efficient insertion of the spacer.

The shape of the protrusions or teeth 46 also may be varied to facilitate more efficient insertion of the spacer 30 while still maintaining the ability to securely hold the spacer in its proper position after surgery. For instance, a region of protrusions 48 near the leading edge or near a chamfered or tapered lip 40 may be preferentially angled or shaped such that they provide less resistance to movement in one direction than another. Preferably, this region of protrusions is less resistant to movement in the direction in which the spacer is inserted. The degree to which the resistance to this direction of movement is lowered may vary. For instance, the protrusions 46 may resist movement in one direction by less than about 80 percent of the resistance provided by the protrusions in the opposite direction. Alternatively, the resistance to movement in one direction may be 50 percent or less of the resistance to movement in the opposite direction.

Figure 2A:
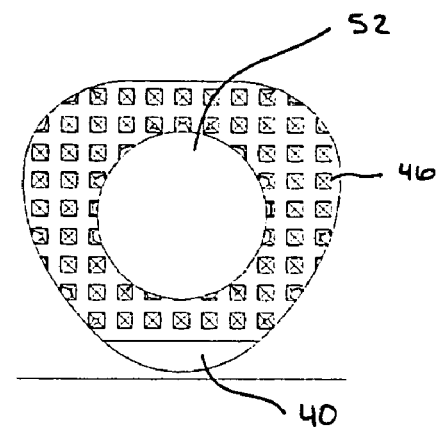
FIGS. 2A–C are variations of top plan views of the fusion spacer of FIG. 1.

In this manner, spacers 30 of the present invention may have a transition region 48 of protrusions disposed between a chamfered or tapered lip and a region of protrusions that are neutral with regard to the degree to which they resist movement, as shown, for example, in FIGS. 2A and 7B. The width of this transition may vary. In one embodiment, the transition region is from about 1 mm to about 8 mm wide when measured in the direction of travel of the spacer during insertion. The width of the transition region may also be from about 0.4 mm to about 1.5 mm, and in another embodiment it may be from about 0.6 mm to about 1.0 mm wide. Alternatively, the width of the transition region may be described by the number of rows on a surface of a spacer that have preferentially angled protrusions. In one embodiment, for instance, the transition region 48 may be formed of two or more rows of angled protrusions.

In another embodiment, a transition region 48 may form part of all of a perimeter region of protrusions near or around all or part of the outermost edges of the upper and lower surfaces 42, 44 of the spacer 30 may have preferentially less resistance to movement in one or more directions. This embodiment is further illustrated in FIGS. 2A and 7B. The width of the perimeter region may be from about 1 mm to about 8 mm. The height of the protrusions in the transition region also may be higher than the regions where the protrusions are neutral so that the spacer initially rides more on the chamfered or tapered lip, if present, and on the preferentially oriented protrusions during insertion. In one embodiment the average height of the preferentially oriented protrusions are about 10 percent or more higher than the average height of non-preferential, or neutral, protrusions. In another embodiment, the preferentially oriented protrusions have an average height that of at least about 15 percent greater than the average height of non-preferential protrusions.

Figure 5:
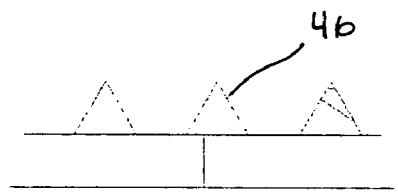
FIG. 5 is an enlarged partial side view of protrusions of the fusion spacer of FIG. 1.
Figure 11A:
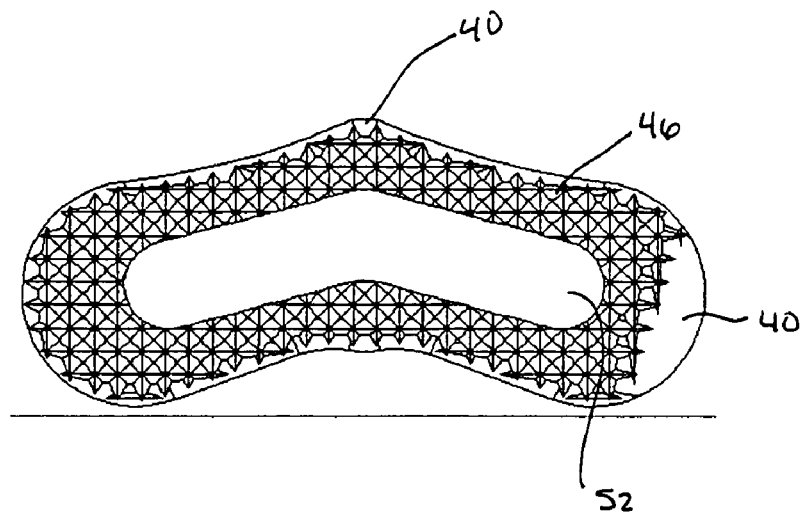
FIGS. 11A–F are variations of top plan views of the fusion spacer of FIG. 10.

As mentioned above, the overall configuration, distribution, and number of protrusions may vary depending on the intended location in the spine where the spacer may be inserted. For instance, some or all of the protrusions may have a sawtooth configuration having substantially symmetrical surfaces and angles off of a vertical axis that extends through the peak of the protrusion, such as illustrated in FIG. 5. Alternatively, as described above, the protrusions may have different angles off of the vertical axis so that the protrusions are more resistant to movement in one direction than in the opposite direction. In either case, the angle at which the side or sides of a protrusion extend from the peak to a base may form an angle of about 50° to about 70°, and preferably is about 60°.

The concentration of the protrusions on the spacer surface also may be varied. For instance, a spacer for use in treating the lumbar region of the spine may utilize a greater concentration of protrusions 46 on the upper and lower surfaces 42, 44. In contrast, a spacer for use in treating cervical regions of the spine may have a lower concentration of protrusions.

Not only may the protrusions of a spacer for the cervical region be less concentrated, they also may be smaller in height than the protrusions that might be used on a spacer for the lumbar regions. One benefit a lower concentration of protrusions can provide for treating a cervical region is that there is a greater likelihood that the protrusions will fully or at least substantially extend into and grip the treated area in order to resist movement. In these embodiments, the anatomy in direct contact with the upper and lower surfaces of the spacer may rest substantially against the open areas of the spacer where protrusions are not located.

In contrast, when the spacer is in the lumbar region it may be more beneficial to have a higher concentration of protrusions in order to account for variations in anatomy between different patients. In general, the anatomy of vertebral bodies in the lumbar region may be curved, but the curvature of a vertebral body from one patient to another may vary. By having the protrusions densely packed together, any potential adverse effect on properly positioning the spacer that may result from these differences in curvature can minimized. Once a spacer is positioned within a treated area of the lumbar region of a patient's spine, the curved surfaces of the neighboring anatomy may be applied against the upper and lower surfaces of the spacer. As pressure is increased, the forces applied cause the protrusions to extend into the neighboring anatomy to varying degrees. Thus, if the curvature of the treated area is different from the curvature of the spacer, the portions of the treated area that first contact the spacer may exhibit greater engagement with the protrusions than in other areas.

One way to describe the concentration of protrusions 46 on a spacer 30 may be by the average distance between the peak of a first protrusion to a neighboring one. For instance, a spacer for treating the lumbar region of the spine may have an average peak-to-peak distance of about 0.4 mm to about 2.5 mm. In another embodiment, the average peak-to-peak value is from about 0.7 mm to about 1.0 mm.

Similarly, one embodiment of a spacer 30 for treating the cervical region of the spine may have a peak-to-peak distance of about 0.3 mm to about 2.5 mm, while in another embodiment the distance may be from about 1.0 mm to about 1.5 mm. Preferably, the peak-to-peak distance is about 1.25 mm when the spacer is intended to treat the cervical region of the spine.

Another way to describe the concentration of protrusions 46 on a surface 42, 44 of a spacer is by the average spacing between the bases of a first protrusion to a neighboring one. As protrusions 46 are spread farther apart, the surface of the spacer 30 in between the protrusions becomes larger. Thus, for a spacer for use in treating the cervical region of the spine, the average distance between the bases of the protrusions may be about from 0.1 mm to about 1.5 mm. In other embodiment, the average base-to-base distance between protrusions is from about 0.5 mm to about 1.0 mm. Preferably, the average base-to-base distance between neighboring protrusions is about 0.8 mm.

As mentioned above, the protrusions 46 on a spacer 30 for treating the lumbar region of the spine may be located more closely to each other than the protrusions on a spacer for other regions of the spine. For instance, the average distance between the bases of the protrusions may be from about 0 mm to about 1.0 mm. In another embodiment the average base-to-base distance is less than about 0.5 mm, and more preferably is less than about 0.25 mm.

As discussed above, the height of the protrusions also may be varied according to what region of the spine the treated area is located. Protrusions 46 for treating the cervical region, for example, may be smaller in height than protrusions of a spacer for treating the lumbar region. For a cervical region, the average height of the protrusions generally may be from about 0.3 mm to about 1.0 mm, although in other embodiments the average height is from about 0.4 mm to about 0.8 mm. More preferably, the average height of the protrusions is about 0.6 mm.

When treating the lumbar region of the spine, the average height of the protrusions may be from about 0.4 mm to about 1.5 mm. In another embodiment, the average height of the protrusions is from about 0.6 mm to about 1.0 mm. Preferably, spacers for treating the lumbar region of the spine have protrusions that have an average height of about 0.8 mm.

Another feature of the present invention that may result in more efficient insertion or placement of the spacer 30 concerns how the spacers may receive instrumentation for manipulation and insertion of the spacer into its proper position. As mentioned above, conventional tooling for manipulating the spacer requires that there be greater clearances in the treated area than needed for the spacer alone in order to accommodate the portions of the tooling that extend beyond the surface of the spacer. In contrast, some embodiments of the present invention do not require an insertion area that is larger than the spacer. Thus, in a preferred embodiment the spacer has at least one, but more preferably two or more tooling engagement surfaces 48, 50 disposed on opposing surfaces of the spacer. The spacer is thereby capable of being manipulated or inserted into position by gripping the engagement surfaces with a suitable tool.

For instance, one example of a suitable gripping tool may be a device having a plurality of arms that may be selectively expanded or opened and subsequently closed or compressed onto the engagement surface. In one embodiment, the engagement surface is formed from plurality of channels formed in the spacer. Preferably, there is a channel located at each engagement surface in which the arms of the manipulating or insertion tool may be disposed to further help ensure that the tooling does not project beyond the largest cross-sectional view of the spacer when viewed along the direction in which the spacer will travel during insertion.

In some cases, the tooling engagement surfaces are disposed on the top and bottom surfaces of the spacer as illustrated, for instance, in FIGS. 14 and 15A–C. The direction of the engagement surface may be selected according to the intended approach for inserting the device. For example, the engagement surfaces may be configured to extend in a generally posterior-anterior direction. In other embodiments, the engagement surfaces may be configured to extend in a lateral direction or in an anterolateral direction.

Once the spacer 30 has been moved into position, it is desirable for it to have sufficient structural rigidity or integrity that the spacer does not buckle or otherwise fail under loading by the spine. In general, the spacer should be configured so that it meets requirements for axial compression, axial torsion, subsidence, and resistance to expulsion. As used herein, structural rigidity or integrity refers to the capability of the spacer to resist axial compression and axial torsion without buckling or otherwise failing.

In order to minimize the risk of failure from compressive or torsional loading, it is preferred that the spacer 30 meets or exceeds minimum structural rigidity values. In general, it is preferred that the rigidity of the spacer exceeds the rigidity of the neighboring vertebral bodies to ensure that the spacer does not collapse or fail under loading conditions first. For instance, in one embodiment the spacer is capable of bearing axial compression loads of about 10 kN or more, while in another the spacer is capable of undergoing axial compression loading of about 15 kN or more. In general, increases in rigidity often can lead to larger bulk or size of the spacer. Thus, while the spacer should be sufficiently rigid to withstand expected loading conditions, eventually the benefits of increasing rigidity become outweighed by other disadvantages such as overall size of the spacer or its ability to provide through holes for promoting fusion. For example, in one embodiment, the spacer 30 is capable of bearing axial loads of about 30 kN or less, while in another the spacer is capable of withstanding about 25 kN or less of axial compression. Additionally, these upper and lower limits may be combined in any manner desired. For instance, a spacer of the present invention may be capable of bearing axial compression loads from about 10 kN to about 30 kN, from about 15 kN to about 25 kN, or from about 10 kN to about 25 kN.

Likewise, the spacer 30 may be capable of resisting torsional loading at least to the degree of torsional resistance that a healthy disc could provide. In one embodiment, the spacer is capable of resisting about 1.8 N·m or more of torsional loading. More preferably, however, the spacer is capable of resisting about 40 N·m or more of torsional loading.

In addition to having structural rigidity or integrity, the spacer 30 should be configured so that it subsides in a desired position without substantially sinking into or piercing nearby anatomy when subjected to axial loading. Different regions of the spine have different sized vertebral bodies, each of which may be subjected to different types and amounts of loading. For instance, vertebral bodies in the lumbar region of the spine are generally larger than vertebral bodies in the cervical region. Typically, the lumbar region of the spine may be subjected to approximately 450 N or more of standing trunk weight, whereas the cervical region may only be subjected to about 50 N of head weight. The larger size of the vertebral bodies in the lumbar region helps distribute the increased loading over a greater area.

Likewise, the upper and lower or contact areas 42, 44 of spacers of the invention may have different sizes depending upon the region of the spine where the treated area is located. The contact area of an upper or lower surface 42, 44 is the area of the spacer defined by the perimeter of the top or bottom view of the spacer 30 subtracted by the area of any through-holes 52 formed within the surface of this area of the spacer. Thus, contact area corresponds to the surface area of the upper or lower surface of the spacer that is capable of contacting neighboring anatomy.

When a single spacer 30 is used, spacers for treating the lumbar region of the spine may have larger upper and lower contact areas than a spacer for treating the cervical region of the spine. In one embodiment, a spacer for treating the lumbar region of the spine has a contact area of about 125 $mm^2$ or more, and more preferably is about 150 $mm^2$ or more. If through-holes 52 are formed in the upper or lower surfaces 42, 44 of a spacer having these sizes of contact area, their overall area may be from about 30 $mm^2$ to about 90 $mm^2$, and more preferably may be from about 50 $mm^2$ to about 75 $mm^2$. Skilled artisans would recognize, however, that these ranges are illustrative, and that not all embodiments of the invention are limited to overall through-hole areas in these ranges. Additionally, as described in the examples below and illustrated in FIGS. 10–13, in some embodiments the spacer 30 may be configured to have an arched or chevron shape when viewing the top or bottom surface, 42, 44 although the dimensions provided above may be used with other spacer shapes as well.

An arched or curved spacer 30 may have a primary leading edge on or near a lateral side of the spacer that helps the physician insert the spacer into the treated area. In addition, the arched or curved spacer may have a second leading edge formed on the anterior side of the spacer. Both leading edges may be configured with a tapered or chamfered lip aid in insertion of the spacer. With respect to the second leading edge disposed on all or part of the anterior side of the spacer, the tapered or chamfered lip may help guide the spacer into position by enabling the spacer to slide across the anterior lip of an end plate in the treated area. Thus, a portion of the anterior edge or lip of the spacer may act as a fulcrum that allows the spacer to pivot and translate during insertion.

In another embodiment of the invention, illustrated in FIGS. 14–17, a spacer 30 for treating the lumbar region of the spine may have a contact area of about 300 mm$^2$ or more, and more preferably may be about 350 mm$^2$ or more. If one or more through-holes 52 are provided on the upper or lower surfaces, 42, 44 the overall area of the through-holes may be from about 40 mm$^2$ to about 160 mm$^2$, and more preferably may be from about 90 mm$^2$ to about 130 mm$^2$. While the spacer 30 may be configured to have any suitable shape, in one embodiment the spacer is generally trapezoidal in shape when viewing the top or bottom surface, as shown, for example in FIGS. 15A–C.

Alternatively, two or more spacers may be used in a treated area in the lumbar region of the spine in order to distribute the load over a greater area without requiring a large window or opening through which each spacer will be inserted. For example, two spacers may be used in a treated area, with each spacer having a contact area of about 75 mm$^2$ or more. More preferably, each spacer has a contact area of about 100 mm$^2$ or more. In one embodiment, the spacer may be configured to be generally rectangular in shape. In addition, as shown in FIG. 7, at least a portion of the lateral sides of the spacer may be tapered so that the width of the trailing edge of the spacer is narrower than the leading edge.

As discussed above, spacers for treating the cervical region of the spine may have a smaller contact area. For instance, a spacer for treating the cervical region of the spine may have a contact area of about 50 mm$^2$ or more, and more preferably may have a contact area of about 75 mm$^2$ or more.

The footprint of the spacer 30 is the overall area circumscribed by the outer perimeter of the upper or lower surfaces of the spacer. In other words, the footprint of a spacer is the combination of the contact area and the area of any through-holes 52 for an upper or lower surface 42, 44. In general, however, the shape or size of the outer perimeter of the upper or lower surfaces of the spacer is determined by the approach used to position the spacer and the size of the treated area. A posterior approach, for example, may provide a smaller window or opening than an anterior approach. Likewise, the available free space for placing a spacer in the cervical region of the spine is smaller than the available free space for placing a spacer in the lumbar region. Once the footprint of the spacer has been established, the size of the through-hole may be determined so that the spacer has sufficient contact area. Thus, as the footprint of a spacer increases, the overall area of through-holes formed in the upper and lower surfaces of the spacer may also be increased.

To avoid potential subsidence issues, through-holes extending from the superior surface to the inferior surface of past devices were typically small in size in comparison to the area of the contact surface of the upper and lower surfaces. In some instances, prior designs provided a plurality of small through-holes or openings through which bone fusion was intended to occur. While these designs may provide structural rigidity, they fail to achieve optimum conditions for fusion to occur. In contrast, the present invention allows for a larger opening through which bony ingrowth may occur while minimizing the risk of subsidence.

It is believed that this configuration will promote fusion more successfully than by providing a plurality of smaller openings. In particular, the ratio of the cross-sectional area of the through-hole extending through the top and bottom surfaces of the spacer to the contact area of the upper and lower surfaces is about 2:3 or more. In another embodiment, the ratio of open area to contact area of the upper or lower surface is about 1:1 or greater so that the size of the opening is at least about the same size as the contact area of the upper or lower surface. It should be noted that the present invention does not preclude the addition of two or more openings through which fusion may occur. In instances where more than one opening is provided, however, it is preferred that the relationship between the size of at least one opening and the contact area stated above remains present.

The spacer also may be configured to resist threshold amounts of expulsion forces. For example, a normal disc may be capable of resisting shear stresses up to about 150 N. Therefore, the spacer may be configured to withstand at least the same degree of shear loading without moving out of its desired position. More preferably, however, the spacer is capable of withstanding even greater shear stresses. For example, the disc may be capable of withstanding about 600 N or more of shear loading, and in another embodiment it is capable of withstanding about 900 N or more. This feature of the spacer is primarily dependent on the configuration of the protrusions placed on the upper and lower surfaces of the spacer. Thus, the spacer may be configured to withstand even more shear stress, such as loading of about 1000 N or more.

In addition to having an opening or through-hole extending between the upper and lower surfaces of the spacer, it is desirable to have a pair of openings or windows 54 in opposing sides of the spacer 30. One advantage that may result from having a pair of windows on opposing sides of the spacer is to allow confirmation of whether the treated area is fusing properly. As discussed above, past designs have provided only a limited ability to confirm whether, and to what extent, fusion has occurred. Typically, the area of the openings or windows was small and only one pair of windows were provided. The small openings of prior designs restricted the ability of the physician to determine whether the treated area was properly fusing. In addition to this benefit, it is believed that another advantage of windows of the present invention is that the large openings may promote bony ingrowth.

The present invention significantly improves visibility in at least two ways. First, the size of at least one pair of windows or openings 54 is enlarged to provide a clearer, more complete viewing of the area of interest. Second, some embodiments of the present invention provide two or more pairs of windows or openings so that a physician may view the fusion area from more than one perspective.

When viewing the spacer 30 from a side direction so that a pair of openings 54 are substantially aligned, the area of the opening may be about 5 mm$^2$ to about 70 mm$^2$, and more preferably about 8 mm$^2$ to about 65 mm$^2$ for a spacer capable of treating the cervical region of the spine. For spacers capable of treating the lumbar region of the spine, the size of the at least one window or opening 54 may vary depending on the size and number of spacers used. For example, the spacer design illustrated in FIGS. 6–9 may have at least one window or opening that is about 10 mm$^2$ to about 90 mm$^2$, and more preferably is about 15 mm$^2$ to about 80 mm$^2$ in size. For a spacer design illustrated in FIGS. 10–13 at least one window or opening may be from about 10 mm$^2$ to about 120 mm$^2$, and more preferably is from about 18 mm$^2$ to about 110 mm$^2$. For a spacer design illustrated in FIGS. 14–17, at least one window or opening may be from about 30 mm$^2$ to about 240 mm$^2$, and more preferably is about 40 mm$^2$ to about 210 mm$^2$.

In addition, the size of the opening or window may be expressed in relationship to the area that is blocked by the material forming the spacer when viewed from the same perspective. For example, when viewing an image of a lateral view of a spacer so that a pair of openings 54 are generally in alignment, the visible area provided by the windows or openings of one embodiment may be at least about 20 percent of the area obscured by the spacer material, and more preferably may be about 25 percent or more. In another embodiment, the area of the window or opening is about 50 percent or greater of the area obscured by the spacer material, and in another embodiment the area of the window is approximately the same as the area obscured by the spacer.

The height of a spacer may be varied depending upon the height of the area of the spine that is to be treated. For this reason, a plurality of spacers having varying heights may provided to a physician. This allows the physician to select from a variety of spacer heights during a surgical procedure. In one embodiment, the height of the window also increases as the overall height of each spacer increases, which in turn may change or alter the relationship between the area of the window and the area of the blocked by the material forming the spacer. One alternative way to describe the spacer window size is by the span or horizontal width of the window. For instance, a spacer capable of treating the cervical region of the spine, such as in FIGS. 1–5, may have a window span or horizontal width of about 4 mm or greater. In another embodiment the width or span of the window is from about 5 mm to about 9 mm, and more preferably is from about 6 mm to about 8 mm. The width or span of the window opening preferably is measured when viewing the spacer from a side direction so that a pair of openings or windows 54 are substantially aligned.

As described above, spacer designs capable of treating the lumbar region of the spine may have varying designs, and thus may have window spans that also vary. For instance, the spacer design illustrated in FIGS. 6–9 may have at least one window or opening having a span or width that is about 4 mm or greater. Another embodiment of the invention may have at least one window or opening having a span or width that is about 6.5 mm or greater.

For a spacer design illustrated in FIGS. 10–13 may have at least one window or opening having a span or width of about 7 mm or greater, and more preferably is about 9 mm or greater. In one embodiment, at least one window or opening has a span or width of from about 8 mm to about 14 mm, and more preferably is from about 9 mm to about 11 mm.

For a spacer design illustrated in FIGS. 14–17, at least one window or opening may have a span or width of about 7 mm or greater, and more preferably is about 8.5 mm or greater. In one embodiment, at least one window or opening has a span or width of from about 7 mm to about 18 mm, and more preferably is from about 8.5 mm to about 16 mm.

The direction of the view provided by the windows or openings also may be selected to provide optimum perspectives of the fusion process. In one embodiment, a pair of windows or openings on opposing sides of the spacer provides a lateral view, while in another embodiment a pair of windows or openings provides an anterior-posterior view.

In some embodiments, two or more than pairs of openings or windows may be used to provide greater visibility and/or promote fusion. The position or location of the pairs of openings may vary, but it is preferred that the perspective of at least one pair of windows or openings is substantially different from the perspective of another pair of windows or openings. For instance, the line of sight provided by one pair of windows or openings may differ by at least about 30 degrees from the line of sight of a second pair of windows or openings. In another embodiment, the difference in the line of sight may be about 45 degrees or greater. The difference between the lines of sight between two pairs of windows also may be approximately orthogonal. For instance, one line of sight may generally provide a lateral view of the interior region of the spacer, while a second line of sight may generally provide an anterior-posterior perspective of the interior region.

If the lines of sight intersect at a location within the footprint of the spacer, the intersection of different lines of sight may coincide approximately in the region where fusion is expected to be most prevalent. In other cases where the intersection of the lines of sight falls outside of the footprint of the spacer, the lines of sight may generally converge toward a region where fusion is expected to occur. Thus, providing multiple pairs of windows from different perspectives either can allow either multiple views of a region of particular interest or can expand visibility of a region of interest that might otherwise be blocked by the structure of the spacer.

For example, fusion typically is expected to begin in the anterior region of the treated area. One reason for this may be that the anterior region may undergo more axial loading than the posterior region. The additional pressure in this region may trigger fusion to begin. Thus, the lines of sight may be positioned so that they intersect in an anterior region of the treated area.

Any biocompatible material may be used to form a spacer of the present invention. For example, suitable materials for forming spacers of the present invention may be include, but are not limited to, titanium and other surgical grade metals and metal alloys. Since metals and metal alloys generally are radio-opaque, several of the advantages of providing large openings or windows in order to view the treated area will be apparent when the spacer is made of these materials. In addition, radiolucent materials also may be used to form spacers of the present invention. For example, a substantial portion of the spacer may be formed of Polyetheretherketone (PEEK) polymers or similar materials. A spacer made of PEEK or other radiolucent material may further comprise a pin disposed within the spacer that helps a physician identify the orientation of the spacer during insertion. Other materials likewise may be used to from all or part of the spacers of the present invention. For example, all or a portion of the spacer may be formed of bioresorbable materials that, over time, may be resorbed and replaced by bone.

These and other features are explained more fully in the embodiments illustrated below. It should be understood that in general the features of one embodiment also may be used in combination with features of another embodiment and that the embodiments are not intended to limit the scope of the invention.

Figure 2B:
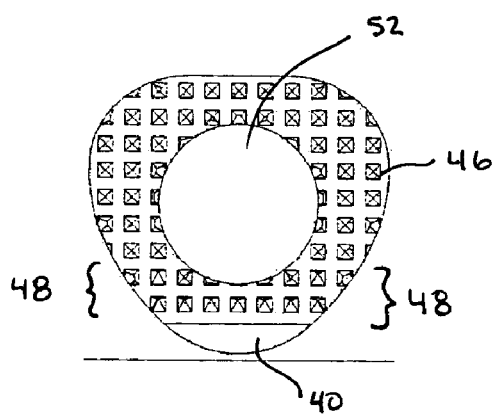
Figure 2C:
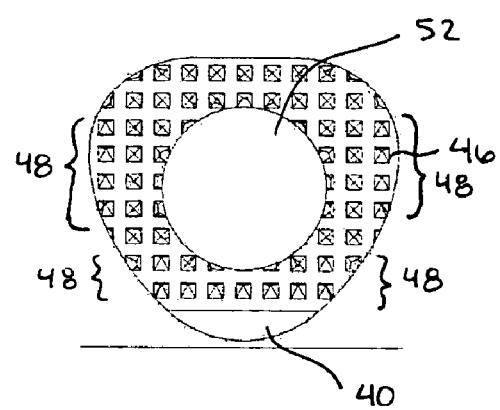
Figure 3A:
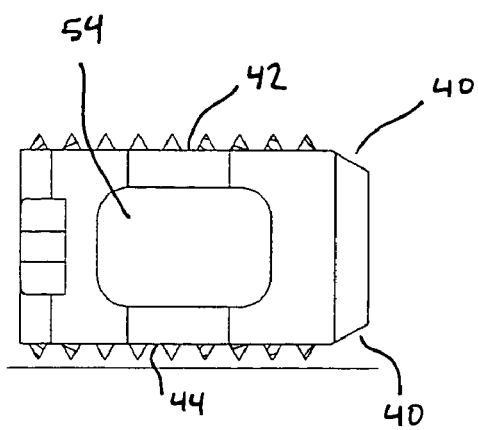
FIG. 3A is a lateral view of one variation of the fusion spacer of FIG. 1.
Figure 3B:
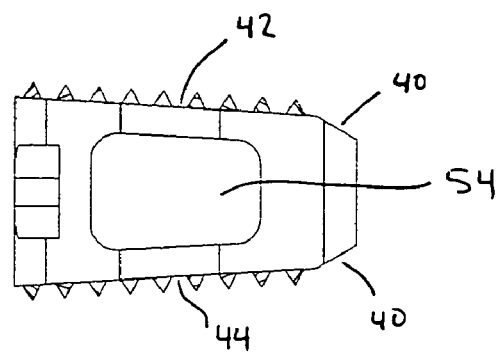
FIG. 3B is a lateral view of a second variation of the fusion spacer of FIG. 1.
Figure 4:
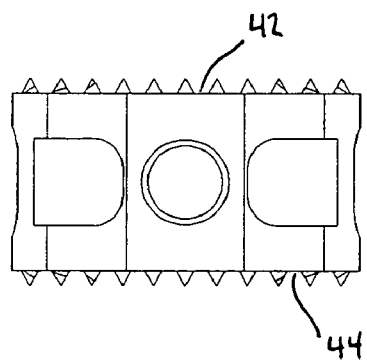
FIG. 4 is an anterior view of the fusion spacer of FIG. 1.

FIGS. 1–4 illustrate one spacer 30 having rounded sidewalls of varying radii of curvature. The anterior, posterior, and lateral sides of the spacer are generally formed from a continuous curved surface. As shown in FIG. 2, the footprint of the spacer may have a teardrop shape that corresponds approximately to the shape of vertebral bodies in the upper thoracic and cervical spine. As shown in FIGS. 1 and 4, the anterior side of the spacer may have a pair of slots and a threaded opening. The slots and threaded opening are configured to receive instrumentation for inserting and manipulating the spacer.

Turning to FIGS. 3A and 3B, the top and bottom surfaces 42, 44 may be configured such that they are substantially parallel to each other as shown in FIG. 3A, or may be angled or tapered with respect to each other such that they diverge as they move further from the chamfered or tapered lip in order to help place the treated area in lordosis.

An oversized through-hole 50 extends through the spacer 30 from the superior to inferior surfaces 42, 44. While the perimeter shape of the through-hole shown in FIG. 2 is generally circular, other shapes also may be utilized to promote fusion in different regions of the treated area. For instance, in any embodiment of the invention the through-hole may be oblong, rectangular, square, trapezoidal, diamond-shaped, slotted, star-shaped, or the like. In addition, the shape of the through-hole may correspond generally to the outer perimeter of the footprint of the spacer. Thus, a spacer having a teardrop footprint may likewise have a teardrop shaped through-hole. Since it is believed that fusion most likely begins in the anterior region of the treated area, the location of the through-hole also may be positioned in this area. Thus, the through-hole need not be centered within the footprint of the spacer.

The area of the through-hole in the embodiment shown in FIG. 2 is approximately 70 percent of the upper or lower surface that contacts and supports nearby vertebral bodies. A skilled artisan would recognize, however, that the size of the opening and the contact area of the spacer may be varied. In one embodiment, the area of the through-hole relative to the contact area is from about 50 to about 90 percent. It is preferred that the relationship between the area of the opening and the contact area of the top or bottom surface corresponds to the ranges previously discussed.

At least one pair of openings or windows may be formed in the sidewalls of the embodiment illustrated in FIGS. 1–4. The area of the opening relative to the area obscured by the spacer when the openings are aligned may be from about 24 percent to about 74 percent.

Turning to FIG. 5, the upper and lower surfaces of the spacer are configures with a plurality of protrusions. The protrusions may be distributed relatively uniformly on the upper and lower surfaces in any suitable manner. For instance, the protrusions may be arranged in a grid pattern as shown in FIG. 2. In another embodiment, the placement of protrusions in one row may be staggered from the placement of protrusions in another row. For instance, the tips of one or more protrusions in one row may be disposed approximately at a location centered between the tips of protrusions from an adjacent row.

The average height of the protrusions may be from about 0.3 mm to about 1.2 mm, and more preferably is from about 0.4 mm to about 0.8 mm. As shown in FIG. 5, the average height of the protrusions is about 0.6 mm. As discussed above, some or all of the protrusions may be preferentially oriented to provide less resistance to movement in one direction than in another. While the embodiment shown in FIGS. 1–5 does not illustrate this feature of the present invention, it would be possible to include it. Instead, the protrusions are shown having a relatively neutral orientation with regard to resistance to movement. The shape of the protrusions may have many different forms, such as a cone or a multi-sided pyramid. Preferably, the base of the protrusion in communication with the upper or lower surface of the spacer is larger than the area of the tip of the protrusion. More preferably, the tips of the protrusions converge to a point.

The angle at which the surfaces of the protrusion converge may vary depending upon the extent and ease to which the protrusions engage with the surfaces they contact. In one embodiment, the angles at which the protrusions converge is from about 30 to about 120 degrees. In another embodiment, the angle is from about 45 to about 90 degrees. As shown in FIG. 5, the protrusions generally have an angle of about 60 degrees.

FIGS. 6–9 illustrate another embodiment of the invention having a generally rectangular, wedge-shaped body. A first set of curved chamfers is provided on the leading edge of the spacer body. In addition to the chamfer being curved, the upper and lower surfaces of the spacer have an arcuate shape extending in the posterior-anterior direction as shown in FIG. 8. Without being bound to any particular theory, it is believed that the arcuate shape of the upper and lower surfaces of the spacer increases the structural rigidity and integrity of the spacer, particularly in areas where large windows or openings are formed in the sidewalls. Here, at least one pair of openings or windows is from about 23 percent to about 45 percent of the area obscured by the spacer when the openings or windows are aligned. In another embodiment, the windows or openings may be from about 55 percent to about 110 percent of the area obscured by the spacer.

As shown in FIGS. 6 and 9, a second set of curved chamfers is provided on the leading edge of the spacer toward the lateral sides of the spacer. Thus, the top, bottom, and side edges of the leading edge of the spacer may be chamfered or tapered.

One or more windows or openings are provided on the each of the sides, front, back, top, and bottom surfaces. As shown in FIG. 8, at least one opening on the sides of the spacer is oversized to promote visibility to the interior region of the spacer where fusion is expected to occur. Likewise, windows or openings on the anterior and posterior sides of the spacer also provide visibility to the fusion area. Thus, the intersection of these lines of sight in this embodiment preferably is disposed toward the anterior region of the treated area where it is believed fusion will most likely occur.

A pair of channels and a plurality of smaller openings on opposing sidewalls of the spacer allow instruments to engage with the spacer during insertion. The sides of the spacer are configured so that the insertion instrument is contained within the maximum width of the spacer, thereby precluding the need for additional space around soft tissue structures.

An oversized, oblong through-hole extends through the spacer from the superior to inferior surfaces. The area of the through-hole in this embodiment is approximately the same as the area of the upper or lower surface that contacts and supports nearby vertebral bodies. The width or length of the opening may be varied to adjust this relationship, or other shapes may be provided for forming the through-hole.

FIGS. 10–13 illustrate another embodiment of the invention having a fusion spacer that has a chevron, arched, or curved shape. In general the mid-portion of the spacer is configured and dimensioned such that it extends toward the anterior of the treated area while the lateral sides of the spacer extend toward the posterior side of the treated area.

This configuration allows for the spacer to be inserted into the treated area using a posterior approach such as described in U.S. Patent Publication No. 2002/0165612 and in U.S. Pat. No. 6,613,090, the entireties of which are incorporated herein by reference.

In several variations of this embodiment of the invention at least one oversized through-hole 52 is disposed on the upper and lower surfaces of the spacer 30. Because of the general shape of the spacer, the through-hole may generally have an inverted v-shape or chevron shape with rounded interior sidewalls at the outermost ends of the through-hole. Alternatively, the through-hole may have a generally arcuate shape on the interior surface of the posterior and anterior sidewalls. The curvature of the through-hole may be selected so that its length corresponds generally to the direction in which the spacer may be inserted. The area of the through-hole in comparison to the contact area of the upper and lower surfaces of the spacer may be from about 50 mm$^2$ to about 75 mm$^2$, while in another embodiment it is approximately 60 mm$^2$ to about 70 mm$^2$. The area of the at least one through-hole may be about 35 percent or more of the contact area of the spacer. More preferably, it is about 40 percent or more of the size of the contact area.

Two through-holes may be used as an alternative to using a single oversized through-hole. For instance, a bridge of material may connect the posterior and anterior sidewalls near the central region. The addition of material in this location may help increase structural rigidity and subsidence.

Several variations of the footprint of the spacer are provided in FIGS. 11A–F. With regard to FIG. 11A, for instance, illustrates a spacer having a generally arcuate posterior side and an anterior side formed from a combination of convex and concave curves.

Figure 11B:
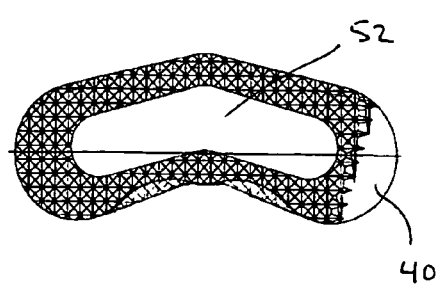

FIG. 11B shows another variation of the footprint where the anterior and posterior sidewalls are formed from two or more linear surfaces connected to convex curved sidewalls on the lateral sides. The central region of the anterior side may be rounded as well where two linear surfaces would converge. Similarly, the posterior side of the spacer of this embodiment also may be formed from two or more linear surfaces connected to the convex lateral sidewalls. The central region of the posterior side near where the linear surfaces would converge may be configured with a bulge formed from a combination of convex and concave curves.

Thickening the contact surface near the lateral sides and near the intersection of the sidewalls that form the posterior side near the region of the spacer where the left and right portions of the posterior sidewalls converge may increase the structural rigidity of the spacer and additionally may aid in improving subsidence. As an alternative, FIG. 11B also illustrates that posterior side may be formed of a combination of convex and concave curves that form a bulge near the central region and narrower contact surfaces in portions of the posterior sidewall. This configuration provides more clearance in the posterior region of the treated area while still achieving desired structural rigidity and subsidence.

Figure 11C:
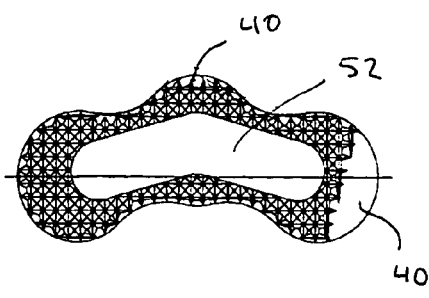

FIG. 11C shows that this alternative to the posterior wall of FIG. 11B may also be applied to the anterior side of the spacer. Thus, in the embodiment shown in FIG. 11C the sidewalls are formed from a substantially continuously curved wall formed from a combination of convex and concave surfaces.

Figure 11D:
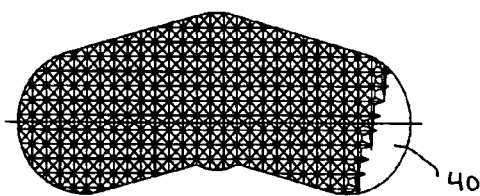

The embodiment shown in FIG. 11D illustrates that the spacer need not have a throughhole disposed in it. The posterior and anterior sides of the spacer illustrated in this embodiment are generally formed from linear surfaces as described above, although the shape of the walls may be curved as described herein or otherwise modified in any suitable manner. The central region of the posterior side also is illustrated as having a bulge or protrusion. As stated previously, this may further improve structural rigidity and subsidence.

Because of the approach used to insert the spacer of this embodiment into position, the primary leading edge of the spacer is located on or disposed near a lateral side of the spacer. As shown in FIG. 10, this leading edge may be configured with a tapered or chamfered lip to aid in inserting the spacer into position. As explained in more detail below, tooling for manipulating and inserting the spacer communicates with the opposing lateral side of the spacer. Thus, as the spacer is pushed into position, the lateral side having the leading edge.

Figure 11E:
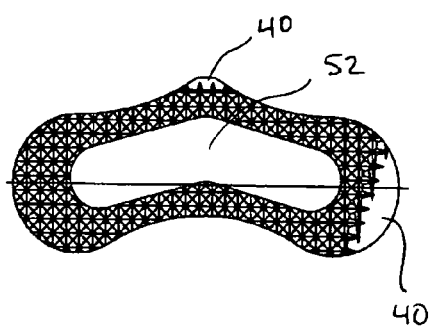
Figure 11F:
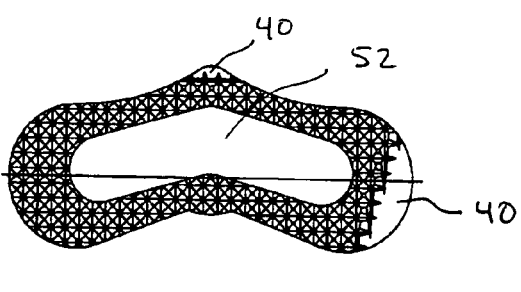
Figure 14:
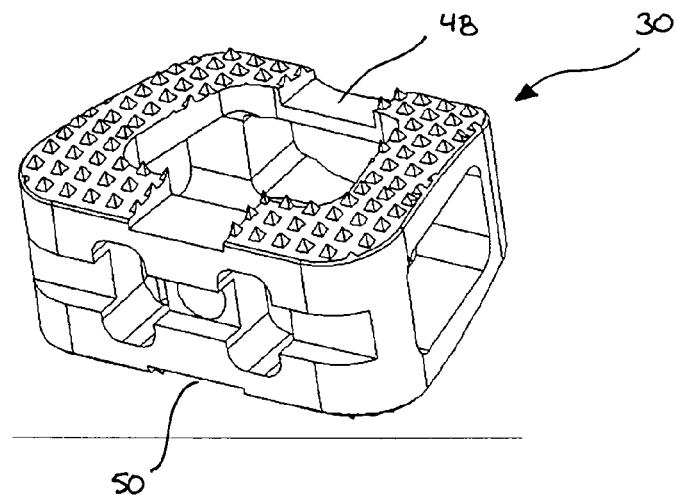
FIG. 14 is a perspective view of another embodiment of a fusion spacer according to the present invention.
Figure 15A:
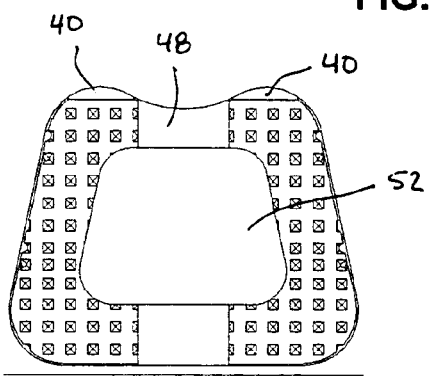
FIGS. 15A–C are variations of top plan views of the fusion spacer of FIG. 14.
Figure 15B:
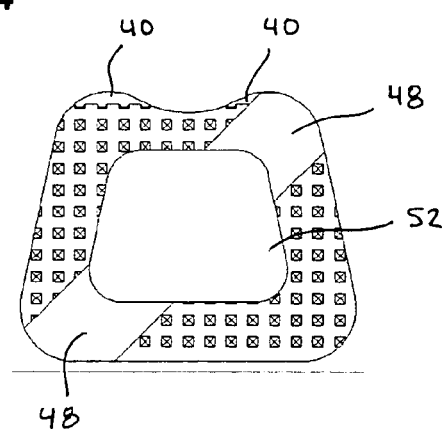
Figure 15C:
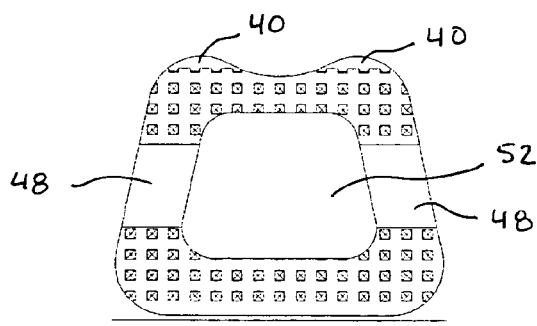

In addition to having a tapered or chamfered lip on the primary leading edge, the spacer of this embodiment of the invention may also have a second leading edge configured with a second tapered or chamfered lip. This feature is illustrated in FIGS. 11E and 11F. In particular, the central region of the anterior side wall may be configured with a lip to help rotate and move the spacer into position. All or a portion of the anterior side may be configured with a tapered or chamfered lip. The tapered or chamfered surface of the lip disposed on the anterior side of the spacer may engage with or pass against an anterior lip of an end plate in the treated area. The lip may then slide against the end plate and guide the spacer into position as it is being inserted.

Figure 12:
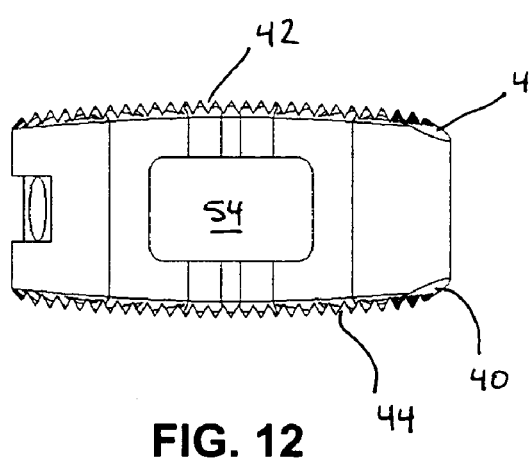
FIG. 12 is a posterior view of the fusion spacer of FIG. 10.
Figure 13:
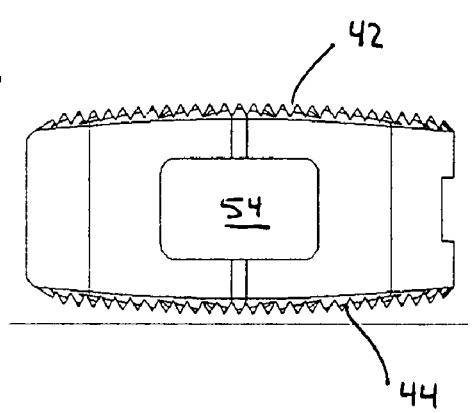
FIG. 13 is an anterior view of the fusion spacer of FIG. 10.

Turning to FIGS. 12 and 13, at least one pair of openings or windows may be disposed on the anterior and posterior sidewalls. Once again, the openings or windows are sufficiently large to provide an unobstructed view of the portion of the spacer where fusion may occur. For instance, in one embodiment of the invention at least one window or opening may be from about 15 mm$^2$ to about 110 mm$^2$. When a pair of windows are aligned, the viewable area of the windows may be from about 30 to 45 percent of the area obscured by the spacer.

In an alternative embodiment, the anterior sidewall may be configured with two openings or windows, both of which may be capable of being selectively aligned with a single opening or window on the posterior sidewall to provide a view of two partially overlapping regions of the through-hole. The placement of the openings or windows may be selected so that the lines of sight of the windows intersect in the anterior region of the treated area. In this alternative embodiment, the central region of the anterior sidewall may form a column that supports the upper and lower surfaces of the spacer.

In addition to providing openings or windows for viewing through the walls of the spacer, an aperture may be provided on a lateral side of the spacer. The aperture may be configured and adapted to receive tooling for manipulating and inserting the spacer into position. In addition, a channel may also be provided on the same lateral side of the spacer. The aperture may then be disposed in a portion of the channel. This configuration provides a relatively flat surface for receiving tooling.

FIGS. 14–18 illustrate yet another embodiment and additional features of the present invention. In this embodiment, the footprint of the fusion spacer is generally trapezoidal in shape with rounded corners and a rounded or curved posterior sidewall. The through-hole on the upper and lower surfaces may also be generally trapezoidal in shape with curved corners as shown in FIG. 15. The area of the through-hole is approximately 30 percent or more of the contact area provided by the upper or lower surfaces of the spacer. For instance, in one embodiment of the invention the through-hole may be about 115 mm$^2$ while the contact area may be about 360 mm$^2$.

Another feature of this embodiment is the presence of channels cut out of the upper and lower surfaces of the spacer. The channels may be used for receiving instrumentation on the upper and lower surfaces of the spacer instead of on the sidewalls as described in other embodiments above. As shown in FIGS. 19A–C, the channels may be configured to allow for lateral, anterolateral, or anterior placement of the spacer. Preferably, the depth of the channels are such that the instrumentation does not increase the profile of the spacer when facing the spacer along the axis or path in which it will follow as it is placed in position.

Figure 16:
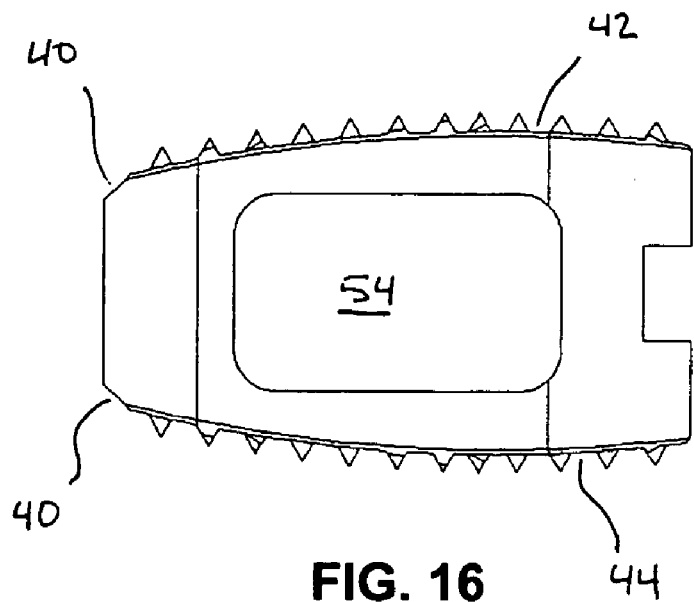
FIG. 16 is a lateral view of the fusion spacer of FIG. 14.
Figure 17:
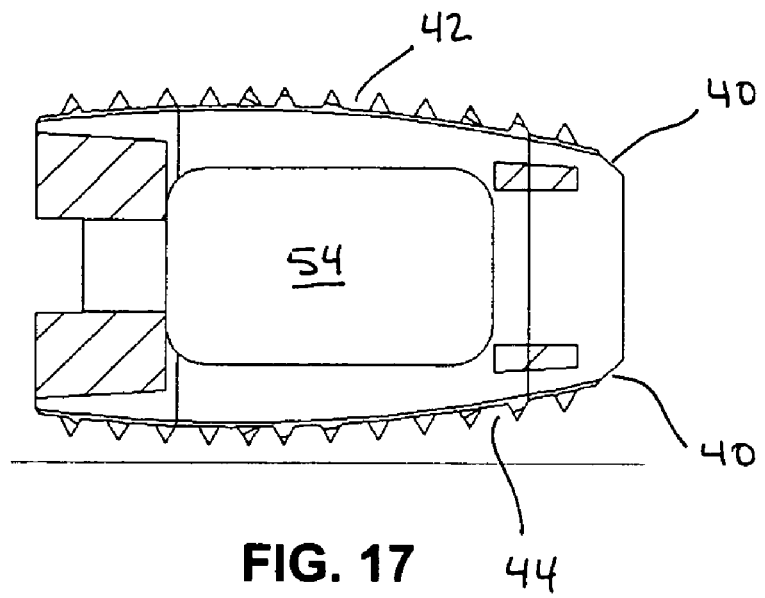
FIG. 17 is a cross-sectional lateral view of the fusion spacer of FIG. 14.

The side view of FIG. 16 further illustrates that the upper and lower surface of the spacer of this embodiment are curved in the anterior-posterior direction. The curvature of the upper and lower surfaces may be selected to help restore or maintain the healthy spinal curvature that would be present in the treated area. In addition, the curvature of the upper and lower surfaces may be configured so that the surfaces intermesh better with the anatomy that they contact.

FIG. 15 illustrates that this embodiment of the invention may have two or more pairs of windows or openings that permit multiple views of the interior region of the spacer. Each pair of openings or windows provides a line of sight. As shown, these lines of sight may be generally perpendicular to each other. By providing visibility to the interior region of the spacer in both the lateral direction and the anterior-posterior direction, the physician is better able to discern the progress of the fusion of the treated area.

Preferably, at least one pair of openings or windows is from about 45 mm$^2$ to about 205 mm$^2$. The area formed by the pair of windows or openings may be about 50 to about 90 percent of the area obscured by the spacer when the windows or openings are aligned.

While it is apparent that the illustrative embodiments of the invention herein disclosed fulfill the objectives stated above, it will be appreciated that numerous modifications and other embodiments may be devised by one of ordinary skill in the art. Accordingly, it will be understood that the appended claims are intended to cover all such modifications and embodiments which come within the spirit and scope of the present invention.

The invention claimed is:

1. An intervertebral fusion cage for implantation in a treated area of an intervertebral space between vertebral bodies of a spine, wherein said fusion cage comprises:

a spacer body comprising an inferior surface and a superior surface,
wherein the inferior and superior surfaces each have a contact area capable of engaging with anatomy in the treated area, and
wherein said inferior and superior surfaces define a through-hole extending through the spacer body;

a sidewall disposed between the inferior surface and the superior surface of the spacer body, wherein the sidewall defines at least a portion of an outer perimeter of the spacer, wherein the outer perimeter has a generally arcuate posterior side and an anterior side formed from a combination of convex and concave curves;

a first window having a first area formed in said sidewall,
wherein the first window extends from a first side of said spacer body to a second side along a first window axis, thereby forming a second window having a second area in the second side,
wherein the first and second windows are capable of permitting confirmation that the vertebral bodies in the treated area are fusing together, and
wherein when viewing the spacer body along the first window axis the first window area is about 20 percent or more of the visible area of the first side when viewed from the first window axis;

a first leading edge comprising a chamfer along a portion of a lateral side for insertion of the spacer into the treated area using a posterior approach, wherein the first leading edge is substantially free of protrusions; and a second leading edge comprising a chamfer along a portion of an anterior side, wherein the second leading edge is substantially free of protrusions and is configured to slide against an anterior lip of an end plate of a vertebral body in the treated area and guide the spacer into position as it is being inserted, and wherein a portion of the anterior side is configured to act as a fulcrum to facilitate pivoting and translation during insertion.

2. The intervertebral fusion cage of claim 1, wherein said contact area comprises a plurality of protrusions capable of engaging with anatomy in the treated area once said fusion cage is positioned within the spine.

3. The intervertebral fusion cage of claim 1, wherein the area of the through-hole is about 30 percent or more of the contact area of the inferior surface.

4. The intervertebral fusion cage of claim 3, wherein the area of the through-hole is about 40 percent or more of the contact area of the inferior surface.

5. The intervertebral fusion cage of claim 4, wherein the area of the through-hole is about 50 percent or more of the contact area of the inferior surface.

6. The intervertebral fusion cage of claim 3, wherein said contact area is about 75 mm$^2$ or more.

7. The intervertebral fusion cage of claim 4, wherein said contact area is about 50 mm$^2$ or more.

8. The intervertebral fusion cage of claim 5, wherein said contact area is about 125 mm$^2$ or more.

9. The intervertebral fusion cage of claim 5, wherein said contact area is about 300 mm$^2$ or more.

10. The intervertebral fusion cage of claim 1, wherein said first window axis extends approximately in an anterior-posterior direction.

11. The intervertebral fusion cage of claim 1, wherein the outer perimeter of said fusion cage is generally arch shaped.

12. The intervertebral fusion cage of claim 1, wherein when viewing the spacer body along the first window axis the first window area is about 30 percent or more of the visible area of the first side when viewed from the first window axis.

13. The intervertebral fusion cage of claim 1, wherein when viewing the spacer body along the first window axis the first window area is about 50 percent or more of the visible area of the first side when viewed from the first window axis.

14. The intervertebral fusion cage of claim 1, wherein said spacer body is formed substantially from a radiolucent material, said spacer body further comprising a radio-opaque marker capable of indicating the orientation or position of the fusion cage.

15. The intervertebral fusion cage of claim 1, wherein the though-hole has a generally arcuate shape.

16. The intervetebral fusion cage of claim 15, wherein the curvature of the through-hole extends along a length selected to correspond to the direction in which the cage is inserted.

17. The intervetebral fusion cage of claim 1, wherein the posterior side includes a central region configured with a bulge formed from a combination of convex and concave curves.

* * * * *